US012622652B2

(12) United States Patent (10) Patent No.: US 12,622,652 B2

Hofmann (45) Date of Patent: May 12, 2026

(54) METHOD FOR PROVIDING TRIGGER INFORMATION IN MEDICAL RADIOLOGY

(71) Applicant: Siemens Healthineers AG, Forchheim (DE)

(72) Inventor: Christian Hofmann, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 235 days.

(21) Appl. No.: 18/616,535

(22) Filed: Mar. 26, 2024

(65) Prior Publication Data

US 2024/0324972 A1 Oct. 3, 2024

(30) Foreign Application Priority Data

Mar. 31, 2023 (EP) ..................................... 23165937

(51) Int. Cl.

| *A61B 6/03* | (2006.01) |
| *A61B 6/00* | (2024.01) |
| *A61N 5/10* | (2006.01) |

(52) U.S. Cl.

CPC .............. *A61B 6/03* (2013.01); *A61B 6/5217* (2013.01); *A61B 6/541* (2013.01)

(58) Field of Classification Search

CPC ......... A61B 6/03; A61B 6/5217; A61B 6/541; A61B 6/0487; A61B 6/032; A61N 5/1068; A61N 5/1049; A61N 5/1067; A61N 5/107

See application file for complete search history.

(56) References Cited

U.S. PATENT DOCUMENTS

| 10,779,790 | B2 | 9/2020 | Hofmann | |
| 2008/0212737 | A1* | 9/2008 | D'Souza | .............. A61N 5/1049 |
| | | | | 378/65 |
| 2014/0072097 | A1 | 3/2014 | Mukumoto | |
| 2017/0238895 | A1* | 8/2017 | Hofmann | ............... A61B 5/087 |
| 2018/0185671 | A1 | 7/2018 | Filiberti et al. | |
| 2020/0121266 | A1 | 4/2020 | Hofmann | |

FOREIGN PATENT DOCUMENTS

JP        2019030410 A        2/2019

OTHER PUBLICATIONS

Thomas D. et al.:"A Novel Fast Helical 4D-CT Acquisition Technique to Generate Low-Noise Sorting ArtifacteFree Images at User-Selected Breathing Phases" 2014, www.redjournal.org.

* cited by examiner

*Primary Examiner* — Courtney D Thomas

(74) *Attorney, Agent, or Firm* — Harness, Dickey & Pierce, P.L.C.

(57) ABSTRACT

A computer-implemented method for providing trigger information in medical radiology, comprises: receiving a first portion of breathing signal data; generating movement trigger information regarding a movement of a patient support structure relative to a radiological interaction area based on the first portion of the breathing signal data; providing the movement trigger information; receiving, after providing the movement trigger information, a second portion of the breathing signal data; generating radiation trigger information regarding a release of radiation towards the radiological interaction area based on the second portion of the breathing signal data; and providing the radiation trigger information.

20 Claims, 5 Drawing Sheets

S1 → S2 → S3 → S31 → S4 → S5 → S6 → S61

N 3    3A    3B 2    2M    2X

S1 → S2 → S3 → S4 → S5 → S6

METHOD FOR PROVIDING TRIGGER INFORMATION IN MEDICAL RADIOLOGY

CROSS-REFERENCE TO RELATED APPLICATION(S)

The present application claims priority under 35 U.S.C. § 119 to European Patent Application No. 23165937.6, filed Mar. 31, 2023, the entire contents of which is incorporated herein by reference.

FIELD

In one aspect, one or more example embodiments of the present invention relate to a computer-implemented method for providing trigger information in medical radiology. In other aspects, one or more example embodiments of the present invention relate to a data processing system, to a computed tomography device, to a non-transitory computer program product and to a non-transitory computer-readable storage medium.

BACKGROUND

Breathhold computed tomography (CT) scans can be used in the diagnosis of lung diseases, in particular with regard to pulmonary emphysema, pulmonary fibrosis or chronic obstructive pulmonary disease (COPD). Breathhold, in particular deep inspiration breathhold or deep expiration breathhold, can help to better examine anatomical structures and pathologies. However, breathhold CT is not appropriate for certain groups of patients who are unable to follow instructions, for example infants, young children, unconscious patients or mentally impaired patients. For some of these patients, breathhold may only be achieved by preventing breathing with the help of anesthesia.

US 2017/0238895 A1 discloses a method for respiration-correlated computed tomography (CT) imaging.

US 2020/0121266 A1 discloses a method for carrying out an imaging scan of a patient in a computed tomography system, wherein a respiratory cycle of the patient is acquired.

CT scans, in particular high pitch CT scans, that are performed under free breathing may result in lower image quality, for example due to artifacts caused by uncertainty and/or inconsistency regarding the breathing states being imaged.

SUMMARY

An underlying technical problem of one or more embodiments of the present invention is to facilitate a respiratory triggering in medical radiology that is improved in particular with regard to radiation dose and image quality.

Independent of the grammatical term usage, individuals with male, female or other gender identities are included within the term.

An embodiment of the present invention relates to a computer-implemented method for providing trigger information in medical radiology, the method comprising:

receiving a first portion of breathing signal data, generating movement trigger information regarding a movement of a patient support structure relative to a radiological interaction area based on the first portion of the breathing signal data, providing the movement trigger information, receiving, after providing the movement trigger information, a second portion of the breathing signal data, generating radiation trigger information regarding a release of radiation towards the radiological interaction area based on the second portion of the breathing signal data, providing the radiation trigger information.

The movement of the patient support structure may be translational movement and/or may comprise, for example, an acceleration movement and/or a scan movement, the scan movement occurring later in time than the acceleration movement. The movement of the patient support structure may be parallel to a system axis of the radiological interaction area. The patient support structure may be, for example, a patient table board that is movably mounted on a patient table socket.

The radiation towards the radiological interaction area could be released, for example, by irradiating the radiation by a radiation source and/or by unblocking the radiation by a collimator. The movement trigger information may indicate a start time of the movement of the patient support structure. The radiation trigger information may indicate a start time of the release of the radiation. The breathing signal data may be indicative of a breathing of a patient, in particular a free breathing of the patient. The patient may be located on the patient support structure.

The second portion of the breathing signal data may be indicative of the breathing of the patient during the movement of the patient support structure relative to the radiological interaction area. In particular, the second portion of the breathing signal data may be indicative of the breathing of the patient during the movement of the patient relative to the radiological interaction area, the patient following the movement of the patient support structure. In particular, the first portion of the breathing signal data may be indicative of the breathing of the patient before the movement of the patient relative to the radiological interaction area, the patient following the movement of the patient support structure.

The first portion of breathing signal data may comprise a first time series of breathing signal values, in particular breathing amplitude values. The second portion of breathing signal data may comprise a second time series of breathing signal values, in particular breathing amplitude values, wherein the second time series is later in time then the first time series. In particular, the second time series is later in time then the start time of the movement of the patient support structure, in particular later in time then an end time of the acceleration movement. In particular, the second time series is earlier in time then an end time of the movement of the patient support structure, in particular earlier in time then an end time of the scan movement.

The first check result may be generated by checking, in particular automatically checking, the first portion of the breathing signal data against a first criterion, wherein the movement trigger information is generated based on the first check result, wherein a second check result is generated by checking, in particular automatically checking, the second portion of the breathing signal data against a second criterion, wherein the radiation trigger information is generated based on the second check result.

A fulfillment of the first criterion may indicate, that a deviation of the first portion of the breathing signal data from a first breathing signal reference pattern is below a tolerance level and/or low enough to expect a target breathing state being reached at a timepoint at which an examination area that follows the movement of the patient support structure relative to the radiological interaction area will reach the radiological interaction area.

A fulfillment of the second criterion may indicate, that a deviation of the second portion of the breathing signal data from a second breathing signal reference pattern is below a tolerance level and/or low enough to expect the target breathing state being reached at the timepoint at which the examination area that follows the movement of the patient support structure relative to the radiological interaction area will reach the radiological interaction area. The examination area may comprise, for example, an anatomical structure of the patient.

The first criterion may be related to a first breathing state region, in particular to a first breathing state region of the breathing of the patient, the first breathing state region preceding a target breathing state by a first delay time range, the first delay time range being related to the movement of the patient support structure relative to a radiological inter-action area. The second criterion may be related to a second breathing state region, in particular to a second breathing state region of the breathing of the patient, the second breathing state region preceding the target breathing state by a second delay time range, the second delay time range being related to the release of radiation towards the radio-logical interaction area.

The first delay time range may be related to the time needed for the examination area, that follows the movement of the patient support structure, to reach the radiological interaction area, after the movement of the patient support structure being triggered.

The second delay time range may be related to timing the release of the radiation towards the radiological interaction area around an expected peak of the target breathing state, in particular to cover both flanks of the peak.

The target breathing state may be a maximum inhalation state or a maximum exhalation state. In particular, the target breathing state may be a maximum inhalation state of a specific form or a maximum exhalation state of a specific form, thereby excluding, for example, irregular inhalation states and/or irregular exhalation states. This approach allows maximum inhalation phases and maximum exhala-tion phases being scanned under free breathing with a high "hit-rate", in particular for high pitch helical scans.

The first criterion may be further related to a first tangen-tial region, in particular to a first tangential region of the breathing of the patient, in a velocity-amplitude phase space for the breathing signal data. The second criterion may be further related to a second tangential region, in particular to a second tangential region of the breathing of the patient, in the velocity-amplitude phase space for the breathing signal data.

An initial portion of the breathing signal data may be received, wherein a representative breathing curve is calcu-lated based on the initial portion of the breathing signal data, wherein the first criterion and the second criterion are calculated based on the representative breathing curve, in particular based on a representation of the representative breathing curve in the velocity-amplitude phase space for the breathing signal data.

In particular, the representative breathing curve may be calculated based on a representation of the initial portion of the breathing signal data in the velocity-amplitude phase space for the breathing signal data. In particular, the initial portion of the breathing signal may cover a plurality of breathing cycles. The representative breathing curve may be calculated by applying a machine learning algorithm onto the initial portion of the breathing signal data.

Another embodiment of the present invention relates to a method for respiratory triggering in medical radiology, the method comprising:
   receiving a first portion of breathing signal data,
   generating movement trigger information regarding a movement of a patient support structure relative to a radiological interaction area based on the first portion of the breathing signal data,
   providing the movement trigger information,
   triggering the movement of the patient support structure relative to the radiological interaction area based on the movement trigger information,
   receiving, after providing the movement trigger informa-tion, a second portion of the breathing signal data, in particular, wherein the second portion of the breathing signal data is received after triggering the movement of the patient support structure relative to the radiological interaction area,
   generating radiation trigger information regarding a release of radiation towards the radiological interaction area based on the second portion of the breathing signal data,
   providing the radiation trigger information,
   triggering the release of radiation towards the radiological interaction area based on the radiation trigger informa-tion.

The method may further comprise an acquisition of radiological imaging data, in particular radiological imaging data of the examination area, based on the radiation that is released towards the radiological interaction area, in par-ticular using a fas helical scan.

The second portion of the breathing signal data may be measured during the movement of the patient support struc-ture relative to the radiological interaction area. The breath-ing signal data may be measured, for example, based on a breathing surrogate. The breathing signal data may be mea-sured contact-based, in particular using a chest belt, or contactless, in particular by optical and/or radio-frequency-based methods.

The release of radiation towards the radiological interac-tion area may be triggered during the movement of the patient support structure relative to the radiological interac-tion area. In particular the radiation towards the radiological interaction area may be released during the movement of the patient support structure relative to the radiological interac-tion area.

Another embodiment of the present invention relates to a non-transitory computer program product or a non-transi-tory computer-readable storage medium, comprising instructions which, when the instructions are executed by a computer, cause the computer to carry out the method according to one of the aspects of embodiments of the present invention.

Another embodiment of the present invention relates to a data processing system, comprising a data interface and a processor, the data processing system being configured for carrying out the method according to one of the aspects of embodiments of the present invention.

Another embodiment embodiments of the present inven-tion relates to a medical system, comprising
   the data processing system according to one of the aspects of embodiments of the present invention,
   a breathing signal measurement system for measuring the breathing signal data,
   a radiological device, the radiological device comprising the patient support structure and the radiological inter-action area.

The medical system may be, for example, an imaging system and/or a therapy system. The radiation may be, for example, x-ray radiation. The radiological device may be a computed tomography device.

With this approach the accuracy of prospective respiratory triggering, in particular of high pitch helical CT scans, in case of free breathing patients can be significantly improved, in particular if the breathing is irregular.

Any of the algorithms and/or models mentioned herein can be based on one or more of the following architectures: deep convolutional neural network, deep belief network, random forest, deep residual learning, deep reinforcement learning, recurrent neural network, Siamese network, generative adversarial network or auto-encoder.

The computer program product can be, for example, a computer program or comprise another element apart from the computer program. This other element can be hardware, for example a memory device, on which the computer program is stored, a hardware key for using the computer program and the like, and/or software, for example, a documentation or a software key for using the computer program. A computer-readable storage medium can be embodied as non-permanent main memory (e.g. random-access memory) or as permanent mass storage (e.g. hard disk, USB stick, SD card, solid state disk).

The data processing system can comprise, for example, at least one of a cloud-computing system, a distributed computing system, a computer network, a computer, a tablet computer, a smartphone or the like. The data processing system can comprise hardware and/or software. The hardware can be, for example, a processor system, a memory system and combinations thereof. The hardware can be configurable by the software and/or be operable by the software. Calculations for performing an action of a method may be carried out in the processor.

Data, in particular breathing signal data, can be received, for example, by receiving a signal that carries the data and/or by reading the data from a computer memory and/or by a manual user input, for example, through a graphical user interface. Data, in particular trigger information, can be provided, for example, by transmitting a signal that carries the data and/or by writing the data into a computer memory and/or by displaying the data on a display.

In the context of the present invention, the expression "based on" can in particular be understood as meaning "using, inter alia". In particular, wording according to which a first feature is calculated (or generated, determined etc.) based on a second feature does not preclude the possibility of the first feature being calculated (or generated, determined etc.) based on a third feature.

Reference is made to the fact that the described methods and the described systems are merely preferred example embodiments of the present invention, and that the present invention can be varied by a person skilled in the art, without departing from the scope of the present invention as it is specified by the claims.

BRIEF DESCRIPTION OF THE DRAWINGS

The present invention will be illustrated below with reference to the accompanying figures using example embodiments. The illustration in the figures is schematic and highly simplified and not necessarily to scale.

DETAILED DESCRIPTION

Figure 1:
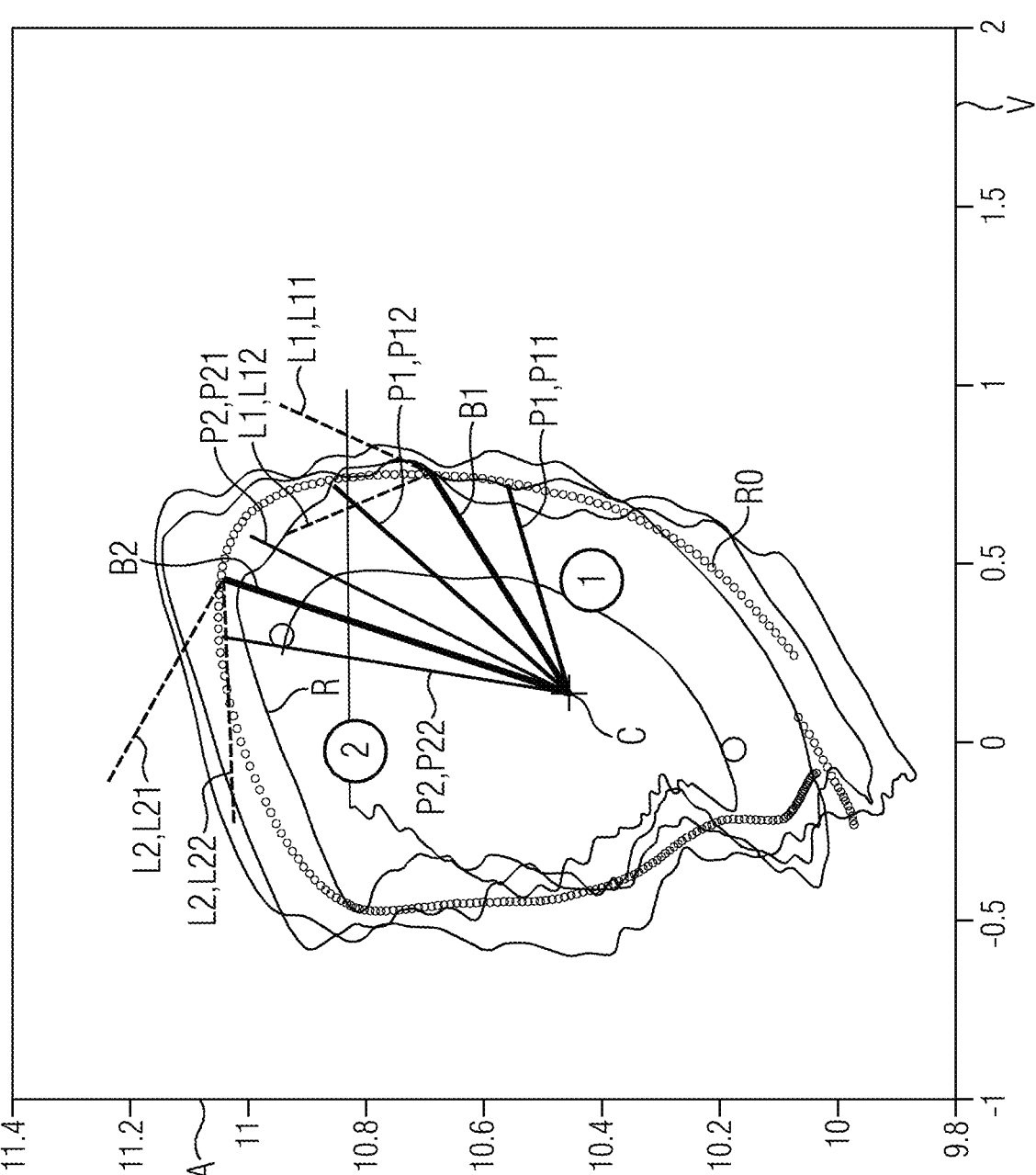
FIG. 1 shows an exemplary velocity-amplitude phase space representation of a patient's breathing.

FIG. 1 shows an exemplary velocity-amplitude phase space representation of a patient's breathing. The breathing signal data are represented by the real time acquired breathing curve R. An initial portion of the breathing signal data is received, wherein a representative breathing curve R0 is calculated based on the initial portion of the breathing signal data, wherein the first criterion and the second criterion are calculated based on the representative breathing curve R0. The representative breathing curve R0 has the center of mass C.

A first check result is generated by checking the first portion of the breathing signal data against a first criterion, wherein the movement trigger information is generated based on the first check result, wherein a second check result is generated by checking the second portion of the breathing signal data against a second criterion, wherein the radiation trigger information is generated based on the second check result, the first criterion being related to a first breathing state region P1, the first breathing state region P1 preceding a target breathing state by a first delay time range, the first delay time range being related to the movement of the patient support structure 14 relative to a radiological interaction area, the second criterion being related to a second breathing state region P2, the second breathing state region P2 preceding the target breathing state by a second delay time range, the second delay time range being related to the release of radiation 27 towards the radiological interaction area. In the case shown in FIG. 1 the target breathing state is a maximum inhalation state. The first criterion is further related to a first tangential region L1 in a velocity-amplitude phase space for the breathing signal data. The second criterion is further related to a second tangential region L2 in the velocity-amplitude phase space for the breathing signal data.

The first breathing state region P1 comprises the breathing state B1 and is confined between the breathing states P11 and P12. The second breathing state region P2 comprises the breathing state B2 and is confined between the breathing states P21 and P22. The first tangential region L1 is confined between the tangents L11 and L12. The second tangential region L2 is confined between the tangents L21 and L22.

The first criterion may be used to determine a timepoint at which the movement of the patient support structure, in particular a table acceleration, will be triggered with the goal, that an examination area that follows the movement of the patient support structure, reaches the radiological interaction area at the same time as the breathing reaches the target breathing state. For example, for fast helical scanning a table acceleration time in the order of 0.5 seconds to 1.0 seconds is needed.

The second criterion may be used to check the breathing just before the examination area that follows the movement of the patient support structure, reaches the radiological interaction area and to prevent the release of the radiation towards the radiological interaction area, if the achievement of the goal, that the examination area that follows the movement of the patient support structure, reaches the radiological interaction area at the same time as the breathing reaches the target breathing state, can no longer be expected, for example due to irregularities in the breathing.

Figure 2:
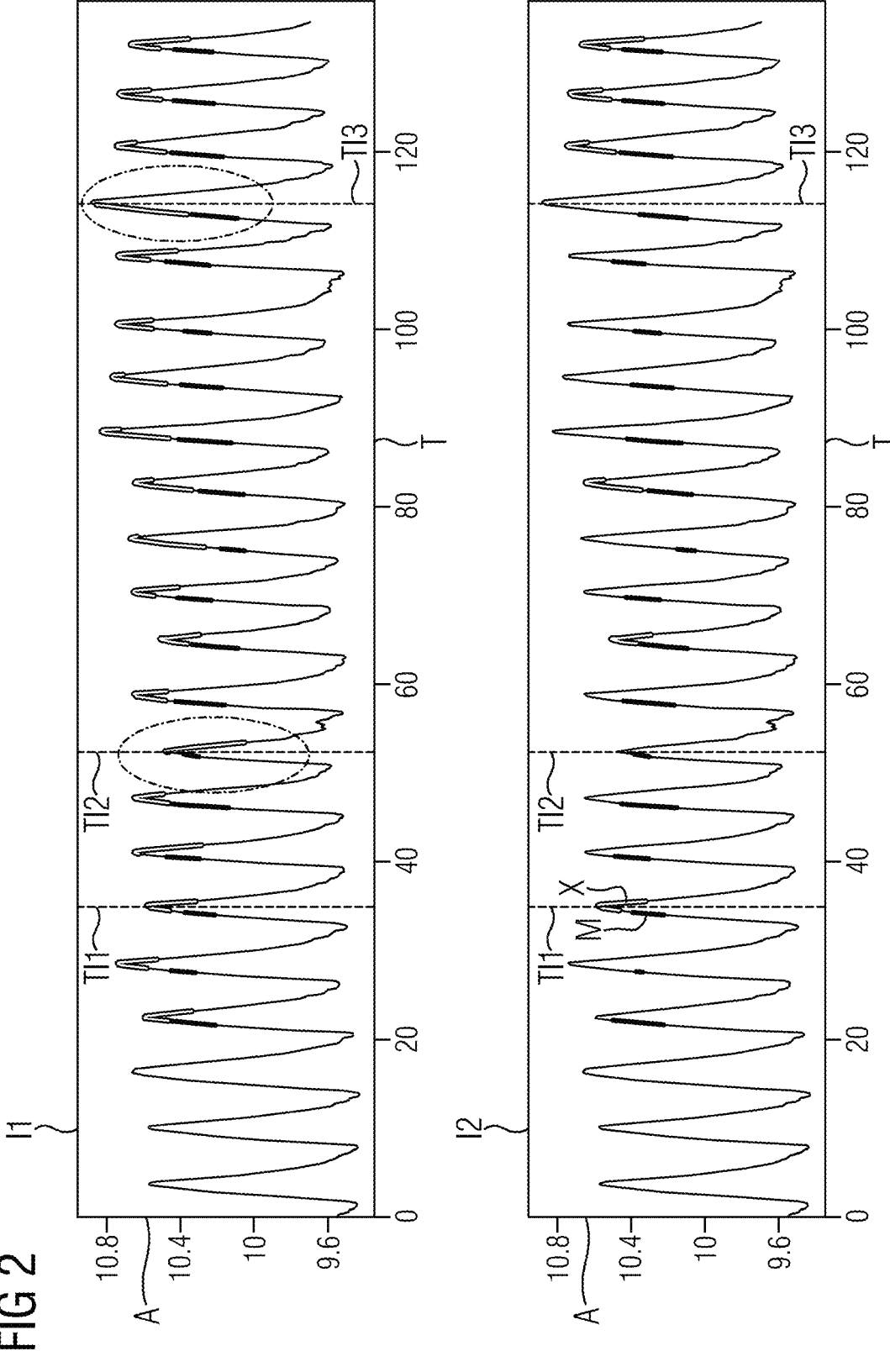
FIG. 2 shows two examples of inhalation triggering.

FIG. 2 shows two examples of inhalation triggering. The breathing amplitude A in arbitrary units is shown versus the time T in seconds. In the first example I1 of the inhalation triggering, only the first criterion is applied. In the second example I2 of the inhalation triggering, both the first criterion and the second criterion are applied.

Marked in black are the regions of the breathing signal curve, for which the first criterion is fulfilled. The movement trigger information is provided immediately after the first sample of such a region is identified. Marked in white are the regions of the breathing signal curve, for which the radiation would be released towards the radiological interaction area. When only the first criterion is applied, radiation would be released also for breathing states that deviate significantly from the desired form as can be clearly seen, for example, for the time points TI2 and TI3. This may cause lower image quality and/or artifacts.

If both criterions are applied, triggering happens more rarely but more consistent and accurate. For example, around the time point TI1 the radiation would be released in a region X that covers both flanks of the maximum inhalation peak, wherein the movement trigger information was provided immediately after the earliest sample of the region M was identified.

Figure 3:
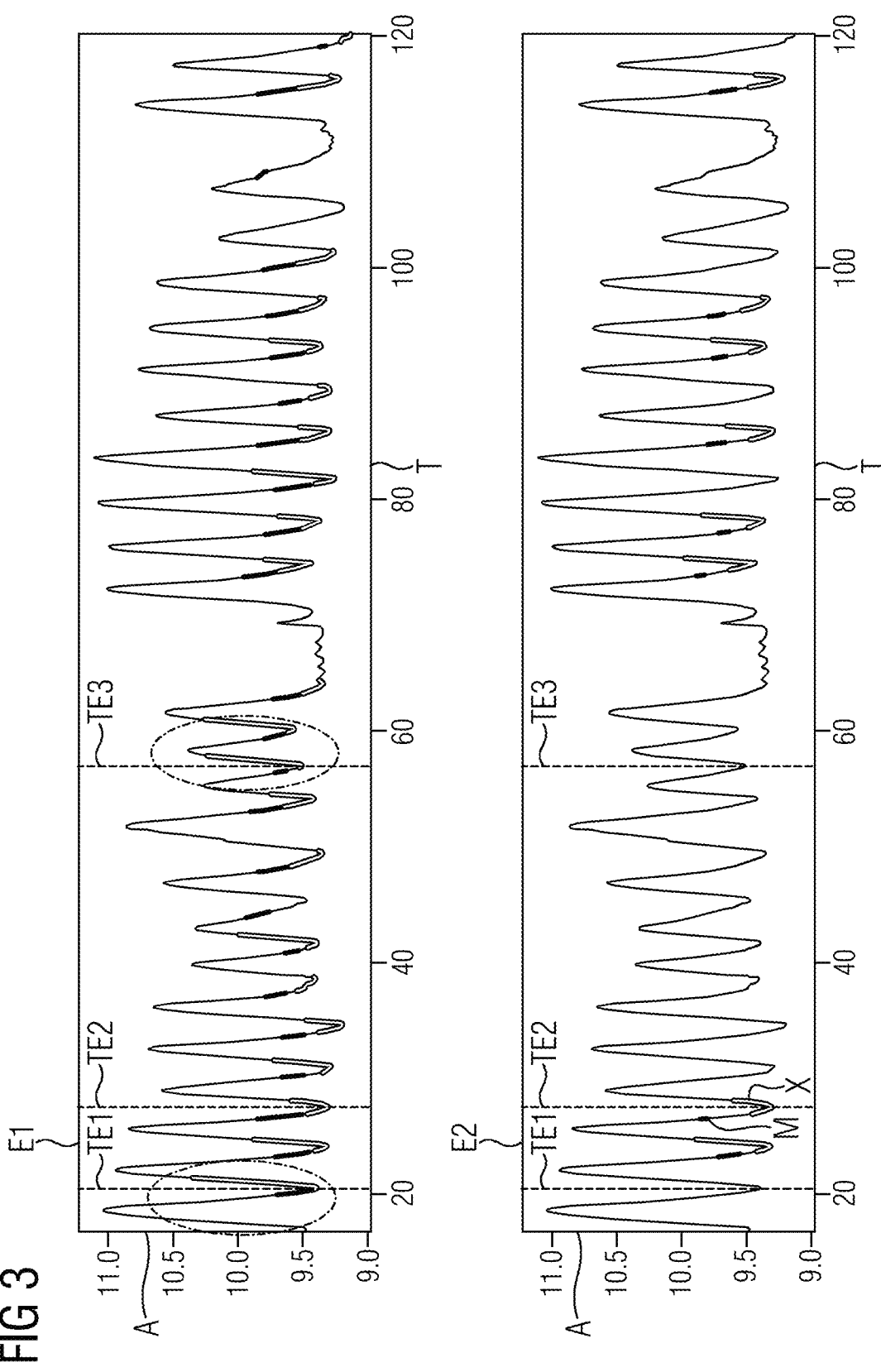
FIG. 3 shows two examples of exhalation triggering.

FIG. 3 shows two examples of exhalation triggering. The breathing amplitude A in arbitrary units is shown versus the time T in seconds. In the first example E1 of the exhalation triggering, only the first criterion is applied. In the second example E2 of the exhalation triggering, both the first criterion and the second criterion are applied. Especially in the comparison of E1 and E2 the advantages of using both criterions get apparent.

When only the first criterion is applied, radiation would be released also for breathing states that deviate significantly from the desired form as can be clearly seen, for example, for the time points TE1 and TE3. This may cause lower image quality and/or artifacts. If both criterions are applied, triggering happens more rarely but more consistent and accurate. For example, around the time point TE2 the radiation would be released for the region X that covers both flanks of the maximum exhalation peak, wherein the movement trigger information was provided immediately after the earliest sample of the region M was identified.

Figure 4:
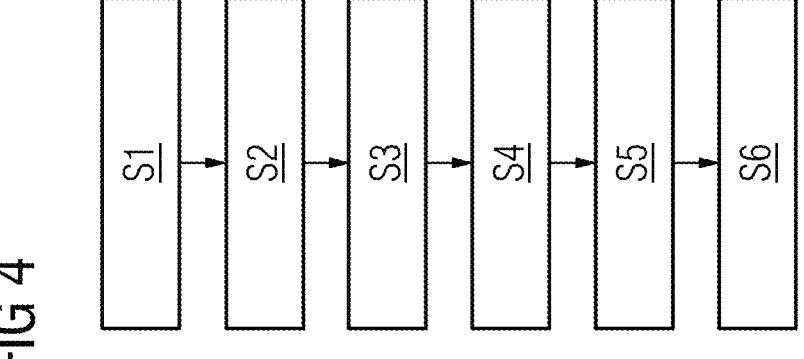
FIG. 4 shows a flow chart for a computer-implemented method for providing trigger information in medical radiology.

FIG. 4 shows a flow chart for a computer-implemented method for providing trigger information in medical radiology, the method comprising:

receiving S1 a first portion of breathing signal data,
  generating S2 movement trigger information regarding a movement of a patient support structure 14 relative to a radiological interaction area 4 based on the first portion of the breathing signal data,
  providing S3 the movement trigger information,
  receiving S4, after providing S3 the movement trigger information, a second portion of the breathing signal data,
  generating S5 radiation trigger information regarding a release of radiation 27 towards the radiological interaction area 4 based on the second portion of the breathing signal data,
  providing S6 the radiation trigger information.

Figure 5:
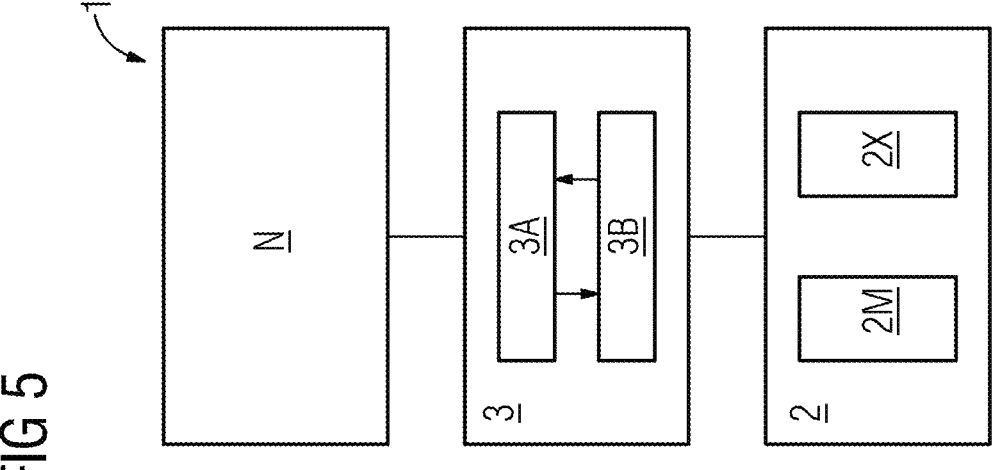
FIG. 5 shows a medical system.

FIG. 5 shows a medical system 1, comprising the data processing system 3 with the data interface 3A and the processor 3B, a breathing signal measurement system N for measuring the breathing signal data and the radiological device 2. The radiological device 2 comprises the patient support driving device 2M for driving the movement of the patient support structure 14 relative to a radiological interaction area 4 based on the first portion of the breathing signal data. The radiological device comprises the radiation release system 2X for releasing the radiation 27 towards the radiological interaction area 4 based on the radiation trigger information. The radiation release system 2X may comprise the radiation source 26 and/or a collimator.

Figure 6:
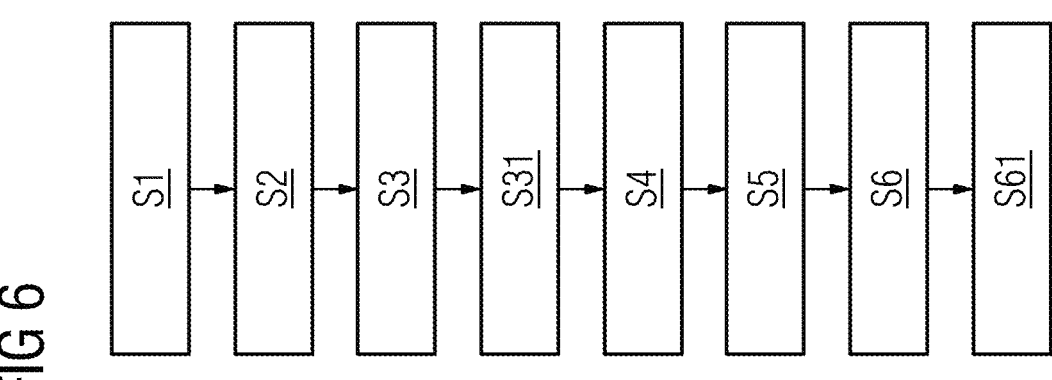
FIG. 6 shows a flow chart for a method for respiratory triggering in medical radiology.

FIG. 6 shows a flow chart for a method for respiratory triggering in medical radiology, the method comprising:

receiving S1 a first portion of breathing signal data,
  generating S2 movement trigger information regarding a movement of a patient support structure 14 relative to a radiological interaction area 4 based on the first portion of the breathing signal data,
  providing S3 the movement trigger information,
  triggering S31 the movement of the patient support structure 14 relative to the radiological interaction area 4 based on the movement trigger information,
  receiving S4, after providing S3 the movement trigger information, a second portion of the breathing signal data,
  generating S5 radiation trigger information regarding a release of radiation 27 towards the radiological interaction area 4 based on the second portion of the breathing signal data,
  providing S6 the radiation trigger information,
  triggering S61 the release of radiation 27 towards the radiological interaction area 4 based on the radiation trigger information.

Figure 7:
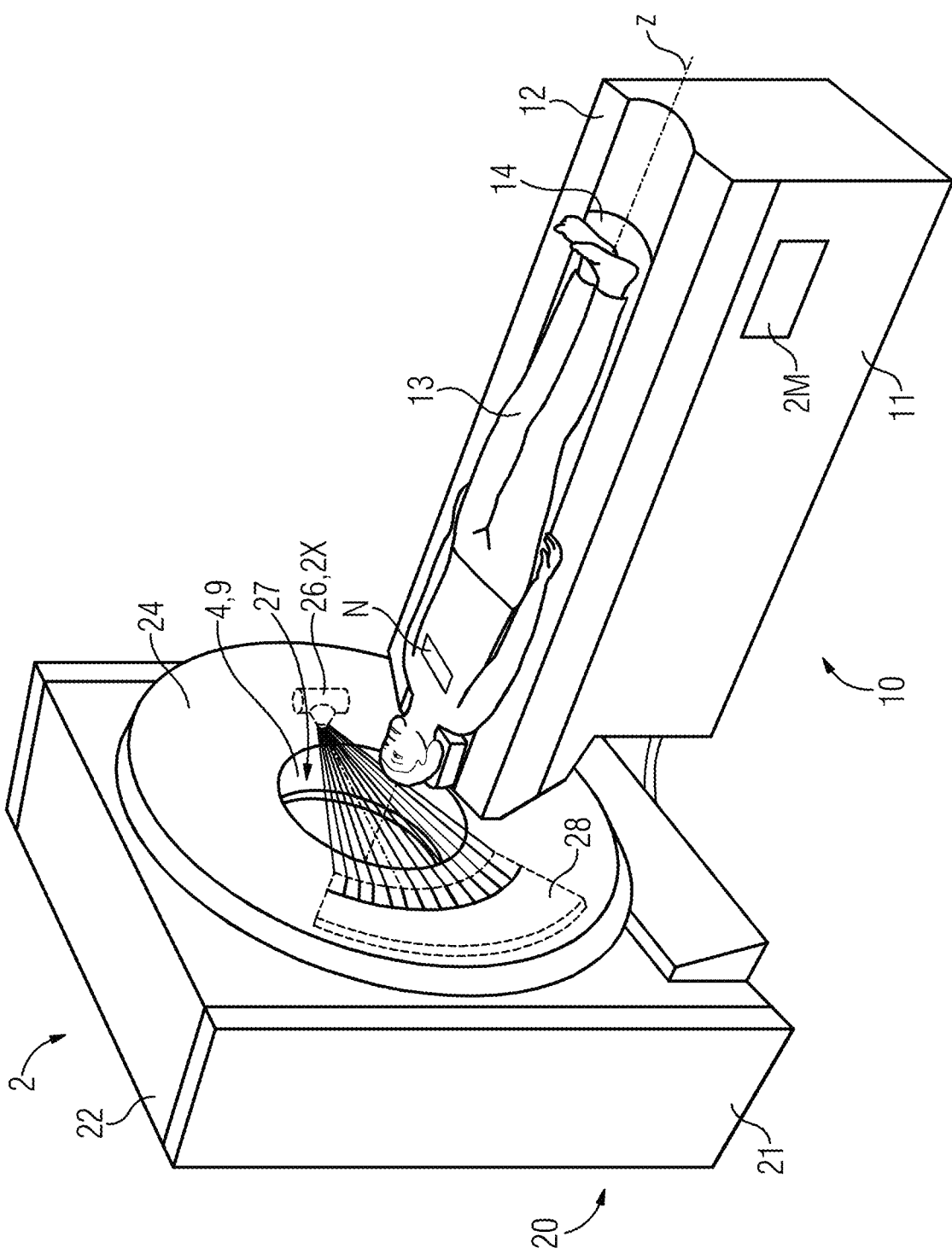
FIG. 7 shows a radiological device.

FIG. 7 shows the radiological device 2 in form of a computed tomography device, comprising the gantry 20, the support frame 21, the tilt frame 22, the rotor 24, the opening 9 for receiving the patient support structure 14, the radiological interaction area 4, the radiological interaction area 4 being located within the opening 9, the radiation source 26 and the radiation detector 28. The radiological device 2 further comprises the patient table 10, the patient table 10 comprising the patient support structure 14 in form of a patient table board. The patient table 10 further comprises the patient support driving device 2M. The patient table board is movably mounted, by a linear guide 12, on the patient table socket 11 along the system axis Z of the radiological interaction area 4. The breathing signal data is indicative of the breathing of the patient 13. The patient 13 is located on the patient support structure 14.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A computer-implemented method for providing trigger information in medical radiology, the computer-implemented method comprising:
   receiving a first portion of breathing signal data;
   generating, based on the first portion, movement trigger information regarding a movement of a patient support structure relative to a radiological interaction area;
   providing the movement trigger information;
   receiving, after providing the movement trigger information, a second portion of the breathing signal data;
   generating, based on the second portion, radiation trigger information regarding a release of radiation towards the radiological interaction area; and
   providing the radiation trigger information.

2. The method according to claim 1, wherein
   the breathing signal data is indicative of a breathing of a patient, and
   the patient is located on the patient support structure.

3. The method according to claim 2, wherein
   the second portion of the breathing signal data is indicative of the breathing of the patient during the movement of the patient support structure relative to the radiological interaction area.

4. The method according to claim 3,
   wherein a first check result is generated by checking the first portion of the breathing signal data against a first criterion,
   wherein the movement trigger information is generated based on the first check result,
   wherein a second check result is generated by checking the second portion of the breathing signal data against a second criterion, and
   wherein the radiation trigger information is generated based on the second check result.

5. The method according to claim 1,
   wherein a first check result is generated by checking the first portion of the breathing signal data against a first criterion,
   wherein the movement trigger information is generated based on the first check result,
   wherein a second check result is generated by checking the second portion of the breathing signal data against a second criterion, and
   wherein the radiation trigger information is generated based on the second check result.

6. The method according to claim 5, wherein
   the first criterion is related to a first breathing state region, the first breathing state region preceding a target breathing state by a first delay time, the first delay time being related to the movement of the patient support structure relative to the radiological interaction area, and
   the second criterion is related to a second breathing state region, the second breathing state region preceding the target breathing state by a second delay time, the second delay time being related to the release of radiation towards the radiological interaction area.

7. The method according to claim 6, wherein the target breathing state is a maximum inhalation state or a maximum exhalation state.

8. The method according to claim 6, wherein
   the first criterion is further related to a first tangential region in a velocity-amplitude phase space for the breathing signal data, and
   the second criterion is further related to a second tangential region in the velocity-amplitude phase space for the breathing signal data.

9. The method according to claim 7, wherein
   the first criterion is further related to a first tangential region in a velocity-amplitude phase space for the breathing signal data, and
   the second criterion is further related to a second tangential region in the velocity-amplitude phase space for the breathing signal data.

10. The method according to claim 6, further comprising:
    receiving an initial portion of the breathing signal data;
    calculating a representative breathing curve based on the initial portion of the breathing signal data; and
    calculating the first criterion and the second criterion based on the representative breathing curve.

11. The method according to claim 5, wherein
    the first criterion is further related to a first tangential region in a velocity-amplitude phase space for the breathing signal data, and
    the second criterion is further related to a second tangential region in the velocity-amplitude phase space for the breathing signal data.

12. The method according to claim 11, further comprising:
    receiving an initial portion of the breathing signal data;
    calculating a representative breathing curve based on the initial portion of the breathing signal data; and
    calculating the first criterion and the second criterion based on the representative breathing curve.

13. The method according to claim 4, further comprising:
    receiving an initial portion of the breathing signal data;
    calculating a representative breathing curve based on the initial portion of the breathing signal data; and
    calculating the first criterion and the second criterion based on the representative breathing curve.

14. A non-transitory computer-readable storage medium comprising instructions which, when executed by a computer, cause the computer to carry out the computer-implemented method of claim 1.

15. A data processing system, comprising a data interface and a processor, the data processing system being configured to carry out the computer-implemented method of claim 1.

16. A medical system, comprising:
    the data processing system of claim 15;
    a breathing signal measurement system configured to measure the breathing signal data; and
    a radiological device including the patient support structure and the radiological interaction area.

17. The medical system according to claim 16, wherein the radiological device is a computed tomography device.

18. A method for respiratory triggering in medical radiology, the method comprising:
    receiving a first portion of breathing signal data;
    generating, based on the first portion, movement trigger information regarding a movement of a patient support structure relative to a radiological interaction area;
    providing the movement trigger information;

triggering the movement of the patient support structure relative to the radiological interaction area, based on the movement trigger information;

receiving, after providing the movement trigger information, a second portion of the breathing signal data;

generating, based on the second portion, radiation trigger information regarding a release of radiation towards the radiological interaction area;

providing the radiation trigger information; and triggering the release of radiation towards the radiological interaction area based on the radiation trigger information.

19. The method of claim 18, wherein the second portion of the breathing signal data is measured during the movement of the patient support structure relative to the radiological interaction area.

20. The method of claim 18, wherein the release of radiation towards the radiological interaction area is triggered during the movement of the patient support structure relative to the radiological interaction area.

* * * * *